(12) United States Patent
Schmidt

(10) Patent No.: US 8,367,866 B2
(45) Date of Patent: Feb. 5, 2013

(54) SINGLE-SOURCE PRECURSOR AND METHODS THEREFOR

(75) Inventor: Wayde R. Schmidt, Pomfret Center, CT (US)

(73) Assignee: United Technologies Corporation, Hartford, CT (US)

( * ) Notice: Subject to any disclaimer, the term of this patent is extended or adjusted under 35 U.S.C. 154(b) by 396 days.

(21) Appl. No.: 12/727,313

(22) Filed: Mar. 19, 2010

(65) Prior Publication Data

US 2011/0230677 A1 Sep. 22, 2011

(51) Int. Cl.
*C07F 5/02* (2006.01)
*C23C 16/00* (2006.01)

(52) U.S. Cl. .................................. 564/8; 427/248.1
(58) Field of Classification Search .... 564/8; 427/248.1
See application file for complete search history.

(56) References Cited

U.S. PATENT DOCUMENTS

| | | | |
|---|---|---|---|
| 4,314,852 A | 2/1982 | Brennan et al. |
| 4,476,164 A | 10/1984 | Veltri et al. |
| 4,481,257 A | 11/1984 | Suplinskas et al. |
| 4,642,271 A | 2/1987 | Rice |
| 5,225,032 A | 7/1993 | Golecki |
| 5,429,870 A | 7/1995 | Kmetz et al. |
| 7,223,465 B2 | 5/2007 | Subramanian et al. |
| 7,510,742 B2 | 3/2009 | Kmetz |
| 2002/0085973 A1 | 7/2002 | Park |

FOREIGN PATENT DOCUMENTS

EP 0424036 4/1991
JP 08311074 A1 * 11/1996

OTHER PUBLICATIONS

Machine Language Translation of JP-08311074 (Jun. 14, 2012).*
Fuller et al., Dalton Transactions, pp. 6381-6392 (2008).*
Wada et al., Journal of Organometallic Chemistry, vol. 485, pp. 127-133 (1995).*
Onodera et al. "Synthesis of Cubic Boron Nitride from Rhombohedral Form Under High Static Pressure," J. Mater. Sci. 25[10] 4279-4284 (1990).
Hirayama et al. "CVD-BN for Boron Diffusion in Si and Its Application to Si Devices," J. Electrochem. Soc., 122 [12] 1671 (1975).
Hanigofsky et al. "Composition and Microstructure of Chemically Vapor-Deposited Boron Nitride, Aluminum Nitride, and Boron Nitride+Aluminum Nitride Composites," J. Am. Ceram. Soc., 74[2] 301-305 (1991).
Nakamura "Preparation and Properties of Amorphous Boron Nitride Films by Molecular Flow Chemical Vapor Deposition," J. Electrochem. Soc., 132[7] 1757 (1985).
Pavlovic et al. "Chemical Vapor Deposition of Boron Nitride Using Premixed Boron Trichloride and Ammonia," J. Mater. Res., 6[11] 2393 (1991).
Kouvetakis et al. "Composition and Structure of Boron Nitride Films Deposited by Chemical Vapor Deposition From Borazine," J. Vac. Sci. Technol. A, 8[6] 3929 (Nov./Dec. 1990).
Gates et al. "Diffusion Effects and Nucleation of Thin Film Boron Nitride Growth From Borazine on the Si(100) Surface," J. Appl. Phys., 72[1] 246 (1992).
Rye "Hot Filament Activated Chemical Vapor Deposition of Boron Nitride," J. Vac. Sci. Technol. A, 9[3] 1099 (May/Jun. 1991).
Devi et al. "Boron Nitride Thin Films on Si(100) by Metal Organic Chemical Vapour Deposition," Solid State Comm., 87[1] 67-70 (1993).
Nakamura "Preparation and Properties of Boron Nitride Films by Metal Organic Chemical Vapor Deposition," J. Electrochem. Soc. 133[6] 1120 (1986).
Yamada "Improvements of Stress Controllability and Radiation Resistance by Adding Carbon to Boron-Nitride," J. Electrochem. Soc., 137 [7] 2242 (1990).
Besmann "Chemical Vapor Deposition in the Boron-Carbon-Nitrogen System," J. Am. Ceram. Soc., 73[8] 2498-501 (1990).
Maya "Aminoborane Polymers as Precursors of Ceramic Materials," Mat. Res. Soc. Symp. Proc., 121, Better Ceramics Through Chemistry III, (1988) 455-460.
Maya "Semiconducting Amorphous Film Containing Carbon, Nitrogen, and Boron," J. Electrochem. Soc. 135[5] 1278-81 (1988).
Maya et al. "Polymeric Cyanoborane, (CNBH2)n: Single Source for Chemical Vapor Deposition of Boron Nitride Films," J. Am. Ceram. Soc. 74[2] 406-409 (1991).
Maya et al. "Pyrolytic Deposition of Carbon Films Containing Nitrogen and/or Boron," J. Am. Ceram. Soc., 73[7] 1912-16 (1990).
Wiberg Naturwissenschaften, 35, 182, 212 (1948).
Hackney, et al. "Organometallic Precursors to AlwSixNyCz Ceramics," in Ultrastructure Processing of Advanced Ceramics, eds. J. D. Mackenzie and D. R. Ulrich, J. Wiley: New York, (1988) 99 and references therein.
May, Leon: "Aminoborane polymers as precursors of C-N-B ceramic materials", Journal of the American Ceramic Society, vol. 71, No. 12, 1988, pp. 1104-1107.
Miele, P., et al: "Borylborazines as new precursors for boron nitride filsm", Journal of Organometallic Chemistry, vol. 690, 2005, pp. 2809-2814.
Partial European Search Report dated Sep. 12, 2011.

* cited by examiner

*Primary Examiner* — Porfirio Nazario Gonzalez
(74) *Attorney, Agent, or Firm* — Carlson, Gaskey & Olds PC

(57) ABSTRACT

A single-source precursor composition includes $R_3B.NX_3$, where B is boron, N is nitrogen, and the R groups and the X groups are selected from hydrogen, alkyl groups, and aryl groups. At least one of the R groups is an alkyl group or an aryl group.

17 Claims, 1 Drawing Sheet

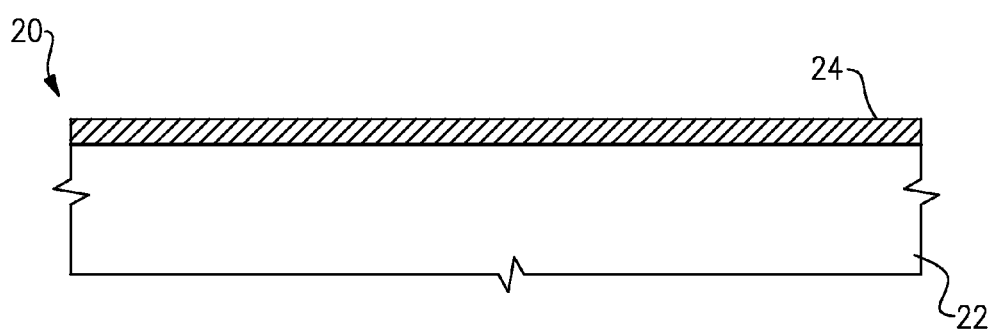

SINGLE-SOURCE PRECURSOR AND METHODS THEREFOR

BACKGROUND

This disclosure relates to precursors for deposition of boron-containing films.

Boron-containing films may be used as coatings on fibers or other substrates for providing oxidation resistance, lubricity, thermal stability, moisture resistance, hardness, or other desirable properties. The boron-containing film may be deposited onto the substrate by vapor deposition from multiple precursors that react in a gaseous state to form the boron-containing coating. As an example, the precursors may include substituted boranes, borazines and/or substituted amines.

SUMMARY

An exemplary single-source precursor composition includes $R_3B.NX_3$, where B is boron, N is nitrogen, and the R groups and the X groups are selected from hydrogen, alkyl groups, and aryl groups. At least one of the R groups is an alkyl group or an aryl group.

An exemplary method of fabricating a single-source precursor composition includes reacting, by adduct formation, a first material of composition $R_3B$ with a second material of composition $NX_3$ to form $R_3B.NX_3$, where at least one of the R groups is an alkyl group or an aryl group.

An exemplary method of forming a boron-nitrogen-carbon film from a single-source precursor composition includes converting $R_3B.NX_3$ to form a first intermediate product $R_2B$—$NX_2$ and a first byproduct RX, converting the first intermediate product $R_2B$—$NX_2$ to form a second intermediate product RB=NX and a second byproduct RX, converting the second intermediate product RB=NX into a third intermediate product $[RBNX]_3$, and converting the third intermediate product $[RBNX]_3$ to form a boron-nitrogen-carbon film.

BRIEF DESCRIPTION OF THE DRAWINGS

The various features and advantages of the disclosed examples will become apparent to those skilled in the art from the following detailed description. The drawings that accompany the detailed description can be briefly described as follows.

FIG. 1 illustrates an example composite article having a boron-nitrogen-carbon film fabricated from a single-source precursor composition.

DETAILED DESCRIPTION OF THE PREFERRED EMBODIMENT

FIG. 1 illustrates selected portions of an example composite article 20. The composite article 20 is not limited to any particular type and may be, for example only, a turbine engine blade or vane, leading edge of an airfoil, a support structure in a turbine engine, a combustor can or liner, a seal, a joint or joining article, a rocket component, or other component over which hot gases pass. In addition the composite article 20 may be a single fiber or filament or a fibrous structure such as a weave, felt or filter or other surface subjected to friction or wear. Alternatively, the composite article 20 may be for any type of application that would benefit from lubricity, hardness, moisture resistance, and/or thermal and/or oxidative stability.

In the illustrated example, the composite article 20 includes a substrate 22 and a boron-nitrogen-carbon layer 24 (e.g., film) disposed on the substrate 22. Generally, the boron-nitrogen-carbon layer 24 ("B—N—C" layer 24) protects the underlying substrate 22 from a high temperature environment and/or corrosive oxidative environmental condition and provides lubricity, hardness or moisture resistance. In this regard, the B—N—C layer 24 may be a coating or film on the substrate 22 or a matrix material of a ceramic matrix composite, and the substrate 22 may be a fiber in a ceramic matrix composite, the body of a component, a barrier layer that is disposed on the body of a component, a matrix in which the B—N—C layer 24 is disposed or any other type of substrate that would benefit from the B—N—C layer 24. In the illustrated example, the B—N—C layer 24 is a continuous layer rather than a discrete region or phase within another material.

The substrate 22 may be a refractory metal-based ceramic material, silicon-based ceramic material or a metallic material, for example. The refractory metal-based ceramic material may be hafnium carbide (HfC), hafnium nitride (HfN), hafnium carbonitride, tantalum carbide (TaC), tantalum nitride (TaN), tantalum carbonitride, zirconium carbide (ZrC), zirconium nitride (ZrN), zirconium carbonitride, niobium carbide (NbC), niobium nitride (NbN), niobium carbonitride, a hafnium-carbon-nitrogen containing material, a tantalum-carbon-nitrogen containing material, a zirconium-carbon-nitrogen containing material, a niobium-carbon-nitrogen containing material, or combinations thereof, including oxygen containing forms of these materials.

The silicon-based ceramic material may be silicon carbide (SiC), silicon nitride ($Si_3N_4$), silicon carbonitride, a silicon-carbon-nitrogen containing ceramic material, or combinations thereof, including oxygen-containing forms of these materials.

In other examples, the substrate 22 may be a metallic material, such as a superalloy. For instance, the superalloy may be a nickel-based or cobalt-based alloy. In any case, the substrate 22 would benefit from additional thermal and corrosion/oxidative resistance for the intended end use. In this regard, the B—N—C layer 24 facilitates improving the thermal and oxidative stability of the composite article 20 and provides lubricity, hardness and/or moisture resistance.

Generally, the B—N—C layer 24 includes boron, nitrogen, and carbon, where there is boron-nitrogen ("B—N") bonding and boron-carbon ("B—C") bonding. The composition of the B—N—C layer 24 may be controlled during processing by controlling a ratio of boron atoms to carbon atoms in a single-source precursor that is used to fabricate the B—N—C layer 24, as will be described in more detail below.

The B—N—C layer 24 may be deposited on to the substrate 22 by depositing a single-source precursor composition. Multi-source precursors react together to form a coating. However, a single-source precursor, as in this disclosure, self-reacts to form a coating without the need to react with another precursor material. Therefore, the single-source precursor serves as the exclusive chemically active starting material.

The disclosed single-source precursors may be vapor deposited, directly deposited, or deposited by any other suitable method. Vapor deposition may be by chemical or physical vapor deposition. Chemical vapor deposition includes volatilizing the precursor and chemically converting the precursor in the volatized state to form the coating. As an example of physical vapor deposition, the precursor may be volatilized and then condensed onto the substrate, followed by a conversion of the condensed species to the coating.

Alternatively, the single-source precursor composition may be directly deposited onto the substrate without being volatilized, such as in a liquid, solid, or semi-solid state. That is, the disclosed single-source precursor composition is not limited to any particular deposition technique and may be compositionally designed for a particularly desired technique.

The single-source precursor composition may be $R_3B.NX_3$, where B is boron, N is nitrogen, and the R groups and the X groups are selected from hydrogen, alkyl groups and aryl groups. At least one of the R groups is an alkyl group or an aryl group. The $R_3B.NX_3$ in this example includes a dative bond between the $R_3B$ and the $NX_3$. As an example, the R and the X may represent the complete chemical group that is bonded to the B or N atom.

The following examples illustrate exemplary compositions of the $R_3B.NX_3$ with regard to the R groups and the X groups. However, it is to be understood that the $R_3B.NX_3$ is not limited to the disclosed examples and, given this disclosure, one of ordinary skill in the art will recognize additional compositions to meet their particular needs.

In some examples, the R groups may be identical and the X groups may be independently identical. For instance, the R groups may be identical alkyl groups and the X groups may independently be identical alkyl groups that are the same or different alkyl groups as the R group. The alkyl groups may be selected from alkyl groups having between 1 and 4 carbon atoms, such as methyl, ethyl, propyl, or butyl. Alkyl groups having greater than 4 carbon atoms may also be used. Alkyl groups having straight chains and/or branched chains may be selected. Alkyl groups having between 1 and 4 carbon atoms may provide the composition $R_3B.NX_3$ with a relatively high vapor pressure that is desirable to vaporize the material for chemical or physical vapor deposition. However, if the vapor pressure of the precursor is not sufficiently high, then there is an option to either heat/warm the precursor to increase its vapor pressure or alternatively, to dissolve the precursor in a suitable solvent and pass carrier gas over or through the solution to provide volatile precursor material. For particular precursor compositions without sufficiently high vapor pressures, it is contemplated that such precursors may be used to create coatings directly using known methods including dip, spray or melt coating methods or solution based approaches.

Alternatively, the R groups may be identical aryl groups and the X groups may independently be identical aryl groups that are the same or different aryl groups as the R group. As an example, an aryl group may refer to any functional group that is derived from an aromatic ring and is not necessarily limited to simple aryl groups, such as phenyl or benzyl.

In some examples, at least one of the X groups may be hydrogen. The other X groups may be alkyl groups or aryl groups as above.

In further examples, at least one of the R groups is an alkyl group and another of the R groups is an aryl group. Likewise, at least one of the X groups may be an alkyl group and another of the X group may be an aryl group.

In a further example, each of the R groups is an alkyl group, but not necessarily identical alkyl groups. It is to be understood that the above examples are exemplary rather than limiting and that combinations of the above examples are contemplated.

The single-source composition $R_3B.NX_3$ may be fabricated by adduct formation. That is, the single-source precursor composition is a product of a direct reaction between distinct molecules resulting in a single reaction product that contains all of the atoms of the source molecules. For instance, a method of fabrication may include reacting, by adduct formation, a first material of composition $R_3B$ with a second material of composition $NX_3$ to form the composition $R_3B.NX_3$. That is, the $NX_3$ directly reacts with the $R_3B$ to form the composition $R_3B.NX_3$ as a product. The conditions of the reaction may depend upon the state and properties of the $NX_3$ and $R_3B$. For instance, if the materials are liquids, the liquids may be mixed together under appropriate thermal conditions. Alternatively, one or both of the materials may be volatilized for the reaction. Alternatively, solid and/or liquid forms of the materials may be dissolved in appropriate solvents for the reaction.

As indicated above, the single-source precursor composition $R_3B.NX_3$ may be vapor deposited onto the substrate 22 to form the B—N—C layer 24. As an example, the process may include converting $R_3B.NX_3$ to form a first intermediate product $R_2B-NX_2$ and a first byproduct RX, converting the first intermediate product $R_2B-NX_2$ to form a second intermediate product RB=NX and a second byproduct RX, converting the second intermediate product RB=NX into a third intermediate product $[RBNX]_3$, and converting the third intermediate product $[RBNX]_3$ to form the B—N—C layer 24. The conversion process includes intentional degradation or decomposition of the starting material with loss of specific byproducts. The conversion process can be induced by radiation based processes including, but not limited to, thermal (e.g. heating), optical (e.g. laser), sonic (e.g. ultrasonic) and microwave processing. The conversion may be conducted under vacuum, in the presence of a carrier gas, such as argon, and at elevated temperatures that are known for vapor deposition. That is, the conversion includes thermally decomposing the single-source precursor. The conversion process may be halted after the desired intermediate product is formed.

The above process may also be illustrated by the below reaction I.

REACTION I:

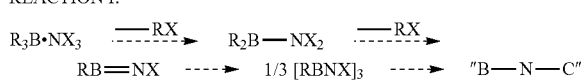

The exemplary single-source precursor composition is also halogen-free. Being halogen-free provides the benefit of avoiding potentially toxic or corrosive or environmentally hazardous byproducts during deposition and formation of the B—N—C layer 24 and also reduces the sensitivity of the precursor to moisture. Additionally, since the single-source precursor composition is halogen-free, there will be no residual halogen atoms in the B—N—C layer 24. Furthermore, in examples that include no boron-hydrogen or nitrogen-hydrogen bonding in the precursor, there would be reduced amounts of boron-hydrogen and nitrogen-hydrogen residual bonding in the B—N—C layer 24 because of the use of the alkyl groups or aryl groups in the single-source precursor.

The composition of a B—N—C layer 24 may be controlled by controlling the composition of the single-source precursor. For instance, using R groups and X groups that are the alkyl groups or aryl groups, rather than using hydrogen, increases the amount of carbon in the B—N—C layer 24. Alternatively, using more hydrogen and less alkyl or aryl groups for the R groups and the X groups reduces the amount of carbon in the final B—N—C layer 24. The number of carbon atoms and the bond type between carbon atoms used in the R groups controls the amount of B—C bonding in the B—N—C layer 24, and the number of carbon atoms and the bond type between carbon atoms used in the X groups controls the amount of N—C bonding in the B—N—C layer 24. Given this description, one of ordinary skill in the art will be able to determine compositions that are suitable for their particular needs.

Although a combination of features is shown in the illustrated examples, not all of them need to be combined to realize the benefits of various embodiments of this disclosure. In other words, a system designed according to an embodiment of this disclosure will not necessarily include all of the features shown in any one of the FIGURE or all of the portions schematically shown in the FIGURE. Moreover, selected features of one example embodiment may be combined with selected features of other example embodiments.

The preceding description is exemplary rather than limiting in nature. Variations and modifications to the disclosed examples may become apparent to those skilled in the art that do not necessarily depart from the essence of this disclosure. The scope of legal protection given to this disclosure can only be determined by studying the following claims.

What is claimed is:

1. A single-source precursor composition, comprising:
$R_3B \cdot NX_3$, wherein B is boron, N is nitrogen, and the R groups and the X groups are selected from a group consisting of hydrogen, alkyl groups, and aryl groups, and at least one of the R groups is an alkyl group or an aryl group, wherein the X groups are independently identical alkyl groups and the R groups are identical alkyl groups.

2. The single-source precursor composition as recited in claim 1, wherein the alkyl groups include between 1 and 4 carbon atoms.

3. A single-source precursor composition, comprising:
$R_3B \cdot NX_3$, wherein B is boron, N is nitrogen, and the R groups and the X groups are selected from a group consisting of hydrogen, alkyl groups, and aryl groups, and at least one of the R groups is an alkyl group or an aryl group, wherein the X groups are independently identical aryl groups and the R groups are identical aryl groups.

4. A single-source precursor composition, comprising:
$R_3B \cdot NX_3$, wherein B is boron, N is nitrogen, and the R groups and the X groups are selected from a group consisting of hydrogen, alkyl groups, and aryl groups, and at least one of the R groups is an alkyl group or an aryl group, wherein at least one of the R groups is an alkyl group and another of the R groups is an aryl group.

5. A single-source precursor composition, comprising:
$R_3B \cdot NX_3$, wherein B is boron, N is nitrogen, and the R groups and the X groups are selected from a group consisting of hydrogen, alkyl groups, and aryl groups, and at least one of the R groups is an alkyl group or an aryl group, wherein at least one of the X groups is an alkyl group and another of the X groups is an aryl group.

6. A single-source precursor composition, comprising:
$R_3B \cdot NX_3$, wherein B is boron, N is nitrogen, and the R groups and the X groups are selected from a group consisting of hydrogen, alkyl groups, and aryl groups, and at least one of the R groups is an alkyl group or an aryl group, wherein each of the R groups is an alkyl group.

7. A method of fabricating a single-source precursor composition, comprising:
reacting by adduct formation a first material of composition $R_3B$ with a second material of composition $NX_3$ to form $R_3B \cdot NX_3$, wherein B is boron, N is nitrogen, the R groups and the X groups are selected from a group consisting of hydrogen, alkyl groups, and aryl groups, and at least one of the R groups is an alkyl group or an aryl group.

8. The method of fabricating as recited in claim 7, wherein the first material and the second material are halogen-free.

9. The method as recited in claim 7, wherein the R groups are identical and the X groups are independently identical.

10. The method as recited in claim 7, wherein at least one of the X groups is hydrogen.

11. The method as recited in claim 7, wherein each of the R groups is an alkyl group.

12. The method as recited in claim 7, wherein at least one of the R groups is an alkyl group and another of the R groups is an aryl group, and at least one of the X groups is an alkyl group and another of the X groups is an aryl group.

13. A method of forming a boron-nitrogen-carbon film from a single-source precursor composition, comprising:
converting $R_3B \cdot NX_3$ by decomposition to form a first intermediate product $R_2B$—$NX_2$ and a first byproduct RX, wherein B is boron, N is nitrogen, and the R groups and the X groups are selected from a group consisting of hydrogen, alkyl groups, and aryl groups, and at least one of the R groups is an alkyl group or an aryl group;
converting the first intermediate product $R_2B$—$NX_2$ by decomposition to form a second intermediate product RB=NX and a second byproduct RX;
converting the second intermediate product RB=NX by decomposition into a third intermediate product $[RBNX]_3$; and
converting the third intermediate product $[RBNX]_3$ by decomposition to form a boron-nitrogen-carbon film.

14. The method as recited in claim 13, wherein the converting of the first intermediate product, the second intermediate product, and the third intermediate product includes thermally decomposing.

15. The method as recited in claim 13, further comprising condensing the $R_3B \cdot NX_3$ onto a substrate.

16. The method as recited in claim 13, further comprising converting the $R_3B \cdot NX_3$ while in a vapor state.

17. The method as recited in claim 13, further comprising converting the $R_3B \cdot NX_3$ while in a non-vapor state.

* * * * *